United States Patent [19]

Bland

[11] 4,199,606

[45] Apr. 22, 1980

[54] PROPIONIC ACID ON A CARRIER MATERIAL AS A PRESERVATIVE

[76] Inventor: Bobby J. Bland, P.O. Box 3891, Corpus Christi, Tex. 78404

[21] Appl. No.: 879,605

[22] Filed: Feb. 21, 1978

Related U.S. Application Data

[63] Continuation-in-part of Ser. No. 835,663, Sep. 22, 1977, abandoned.

[51] Int. Cl.² ................................................ A23B 9/00
[52] U.S. Cl. ..................................... 426/331; 426/97; 426/335; 426/532; 426/807
[58] Field of Search ................. 426/335, 532, 331, 97, 426/807, 654

[56] References Cited

U.S. PATENT DOCUMENTS

| | | | |
|---|---|---|---|
| 2,154,449 | 4/1939 | Hoffman et al. | 426/19 |
| 2,434,204 | 1/1948 | Feachem | 426/335 |
| 3,627,885 | 12/1971 | Rondelet et al. | 424/177 |
| 3,682,653 | 8/1974 | Mommer | 426/654 |
| 3,812,269 | 5/1974 | Mueller et al. | 426/335 |
| 3,836,655 | 9/1974 | Kensler et al. | 424/286 |

FOREIGN PATENT DOCUMENTS

| | | | |
|---|---|---|---|
| 1002977 | 9/1965 | United Kingdom | 426/335 |
| 1346152 | 2/1974 | United Kingdom | 426/335 |

OTHER PUBLICATIONS

Rose et al., Condensed Chemical Dictionary, 7th Edition, Van Nostrand Reinhold Co., 1970, pp. 721, 1003 and 1004.
Zonolite Brand Verxite Granules, W. R. Grace & Co., Brochure G 272 (1965).

*Primary Examiner*—R. B. Penland
*Attorney, Agent, or Firm*—Stewart N. Rice

[57] ABSTRACT

Propionic acid absorbed on a particulate carrier material, including vermiculite and perlite, which will catalyze or effect the formation of monomeric propionic acid in the propionic acid vapors which evaporate therefrom is disclosed as a preservative for various agricultural crop products and derivative and by-products thereof, including animal feeds and cereals.

20 Claims, No Drawings

PROPIONIC ACID ON A CARRIER MATERIAL AS A PRESERVATIVE

The present application is a continuation-in-part of my copending U.S. patent application Ser. No. 835,663, filed Sept. 22, 1977 now abandoned.

BACKGROUND OF THE INVENTION

The present invention relates to the preservation of raw or processed agricultural crop products, and by-products and derivatives thereof, particularly animal feeds and cereals, which are subject to microbiological degradation and mold formation, and which are low in sugars and high in one or more of cellulose, starch and lignin. Thus the present invention is not applicable to preservation of fruits and the like which are high in sugar but is generally applicable to animal foodstuffs, cereal grains, and the like.

It has long been known that propionic acid either alone, or on a carrier material, may be used as a preservative for foodstuffs. The use of propionic acid on a carrier material will generally give better results because of the better distribution of the propionic acid that may be obtained. For examples or prior art usage of propionic acid as a preservative see U.S. Pat. No. 2,154,449 issued Apr. 18, 1939 to C. Hoffman et al; U.S. Pat. No. 3,812,269 issued May 21, 1974 to Mueller et al wherein propionic acid coated on a silica carrier is disclosed; and U.S. Pat. No. 3,836,655 issued Sept. 17, 1974 to Kensler et al wherein propionic acid mixed with sodium methyl dithiocarbamate is disclosed.

Even though much research has been conducted on the use of propionic acid and other compounds as preservatives, the problem of spoilage and mycotoxin formation resulting from fungus (mold) activity is still a big problem in the industry. The discovery of new, useful and more efficient compositions, methods and the like for preservation of products is thus to be desired.

It is thus an object of the present invention to provide a new and useful particulate composition comprising propionic acid on a carrier material which is useful as a preservative. Another object of the present invention is to provide a method of inhibiting fungus growth in products such as animal feeds and cereals by use of such a particulate composition. Still another object of the present invention is to provide an agricultural crop product, or derivatives or by-products thereof, which has improved storage characteristics. Additional objects of the present invention will become apparent from the following description.

SUMMARY

The foregoing and additional objects are accomplished by the present invention which is one of its aspects is a dry, free-flowing particulate composition useful as a preservative for a raw or processed agricultural crop product or by-product or derivative thereof which is subject to microbiological degradation and which is low in sugars and high in one or more of cellulose, starch and lignin, which particulate composition comprises a particulate carrier material having absorbed thereon at least about 0.1 part by weight of propionic acid in the liquid form per part by weight of said particulate carrier material, said particulate carrier material being one which at ambient temperatures within the range of about 0° to 60° C. catalyzes and effects the formation of propionic acid in the monomeric form in the propionic acid vapors which evaporate from time to time from the said propionic acid absorbed on said particulate material. In another aspect the present invention comprises a method for inhibiting fungus growth in such products by use of such a particulate composition. In another aspect, the present invention comprises such a product admixed with such particulate composition.

DETAILED DESCRIPTION OF THE INVENTION

One aspect of the present invention resides in the discovery that use of certain aluminum silicates, particularly vermiculite or perlite, as a carrier material for propionic acid will enable one to obtain increased bactericidal or bacteriostatic and fungicidal or fungistatic action from a given amount of propionic acid. In researching the mechanism by which the use of hydrobiotite provides the increased activity, it was discovered that the vapors which evaporate from a vermiculite carried propionic acid, which vapors provide the bactericidal and fungicidal action, have a greater proportion of propionic acid in the monomeric form and that the monomeric form of propionic acid is the effective species which acts as a bactericidal or fungicidal agent. The fact that the monomeric form of propionic acid, as opposed to the dimeric form, is the effective species has not been known before and its discovery is another aspect of the invention.

In its liquid state, the molecules of propionic acid are very highly associated through hydrogen bonding. That is, the hydrogen of a hydroxyl group of one molecule will be associated with the oxygen atom of a carbonyl group of another molecule. This is known in the prior art. It is also known from the prior art that, in the vapor phase, propionic acid molecules in both the monomeric form and the dimeric form exist in equilibrium, but with the equilibrium being greatly in favor of the dimeric form. For example, see Mathews, D. M. and Sheets, R. W., J. Chem. Soc. (A) (London), pp 2203–2206 (1969) wherein the monomer-dimer distribution of propionic acid in the vapor state is discussed. It is also discussed in such article that surface effect can cause a shift of the equilibrium such that either greater or lesser amounts of monomeric propionic acid are present. As stated above, one aspect of the present invention resides in the discovery of a new way to shift the equilibrium in favor of the monomeric form to effect greater concentration of the monomeric form that heretofore known. The foregoing article by Mathews and Sheets relates only to the chemistry of propionic acid in the vapor phase and does not contain any disclosure that a shift of the equilibrium to favor the monomeric form is desirable in food preservation, nor any other discussion of food preservation. The discovery that the monomeric form of propionic acid is the effective species in food preservation is an aspect of the present invention and heretofore unknown.

When agricultural crop products, cereals, animal foodstuffs and the like are stored, the presence of moisture, even in very small amounts such as the harvest moisture, will cause the product to be subject to microbiological degradation and attacked by mold and fungus. Various additives have been discovered which will serve as a preservative and fungicide, among such being propionic acid. The liquid propionic acid may be sprayed directly onto the product or may first be absorbed on a carrier material which is then admixed with the product. The propionic acid will slowly evaporate during the storage and the propionic acid vapors will provide the bactericidal or fungicidal activity.

The carrier materials disclosed in the prior art all increase the efficiency of the propionic acid by a small amount known as the "carrier effect". It is believed that some of this increase in efficiency when using a carrier is due to better distribution of the propionic acid. The above patent to Mueller et al also discloses that use of silica as a carrier material increases activity because a high evaporation rate of propionic acid is obtained. It has now been discovered that use of certain types of carriers will increase activity of the propionic acid because they catalyze or effect generation of propionic acid in the monomeric form in the propionic acid vapors which slowly evaporate from the propionic acid absorbed on the carrier material.

The present invention may generally be applied to preservation of any raw or processed agricultural crop product, or by-product or derivative thereof, which is subject to microbiological degradation and which is low in sugars and high in one or more of cellulose, starch or lignin. The treatment of fruits is not included and the application of the present invention to fruit preservation is not recommended.

Typical of the products of the type to which the present invention may be applied are hay (baled or pelletized), silage, crop residue such as corn stubble, milo stubble and wheat stubble, spent brewers grain, fishmeal, peanut meal, spent tea leaves, spent coffee grounds, pea shell forage, soybeans, sugar beet pulp, cotton seed hull and meal, sugar cane pulp (bagasse) and cassava root (tapioca). Cereals are also one of the major types of products that may be preserved according to the present invention. The term "cereals" is used herein and in the claims intending to include not only the raw cereal grains themselves but cereal grains which have been processed by chopping, grinding or the like to produce products such as mash, meal and flour. The cereal grains include corn, wheat, rice, barley, sorghum, milo and rye.

The products which may be treated in accordance with the present invention may also contain other additives such as the minerals, vitamins, antibiotics and protein supplements found in many foodstuffs, particularly animal foodstuffs. In fact some of these other additives may be absorbed onto the carrier material utilized in accordance with the present invention along with the propionic acid. The present invention is especially applicable to animal foodstuffs and cereals although not limited thereto. Practically all of the above listed products are used as, or as part of, animal feed although some of such products, such as bagasse from sugar cane, is used in the manufacture of paper and pressboard.

Carrier materials which will provide the desired catalytic effect include those aluminum silicates containing, in addition to the aluminum and silicon, iron and one or more metals selected from the group consisting of the alkaline earth metals and the alkali metals. By the term "alkaline earth metals" is meant magnesium, calcium, strontium and barium, and by the term "alkali metals" is meant lithium, sodium, potassium, rubidium and cesium. These aluminum silicates will be a compound comprised of the following empirical chemical formula:

$$Si_aAl_bFe_cMe_dO_e \qquad I$$

wherein in such formula, O represents oxygen, Si represents silicon, Al represents aluminum, Fe represents iron, and Me represents one or more metals selected from the group consisting of the alkaline earth metals and the alkali metals; and wherein the atomic ratio of the elements in said aluminum silicates are such that when a is 10, b is 2 to 20, c is 0.05 to 15, d is 2 to 20 and e is a number which will satisfy the valence requirements of the silicon and the metals present, the total of c and d not exceeding 25. In the foregoing empirical formula, if Me represents two or more elements, then c means the total numbers of those elements. These aluminum silicates are generally considered to be mixtures of the oxides of the various metals present, such as $SiO_3$ and $Al_2O_3$, but such silicates may actually be coordinate complex structures. There may also, in addition to the metal represented by Me, be minor amounts of other metal cations present in the naturally occuring aluminum silicates, and there may also in some instances be anions present in these aluminum silicates such as hydroxyl ions and/or halide ions.

Such silicates occur naturally but could be synthesized in the laboratory also. Among such aluminum silicates which occur in nature are the micaceous minerals biotite, vermiculite, hydrobiotite, glauconite and some phlogopites. Biotite is of the general empirical chemical formula $K(Mg,Fe)_3(AlSi_3O_{10})(OH)_2$. Glauconite is of the empirical formula $K(Mg,Fe)_2Al_6(Si_4O_{10})(OH)_{12}$ and one form of phlogopite is of the empirical formula $K_2(Mg,Fe)_6Al_2Si_6O_{20}(OH,F)_4$. Frequently, all or a portion of the potassium cations in such empirical chemical formulas are replaced with other metal cations such as calcium, magnesium and the like. In the naturally occurring silicates various other metals may be present in small amounts.

The preferred aluminum silicate for use in the present invention is a vermiculite, especially hydrobiotite which is a form of vermiculite. Vermiculate is the name applied to a group of hydrated magnesium-iron-aluminum silicates of the mica group with chemical composition varying according to the locality from which it is obtained. Vermiculite, including the hydrobiotite form, may be thermally exfoliated (expanded) to result in a product having relatively large pores or capillairies formed between groups of platelets, and this expanded product is preferred in the present invention. The thermal expansion results in a void volume/surface area relationship which would allow greater amounts of propionic acid to be carried. Hydrobiotite which has been thermally expanded is known as verxite and may be readily obtained commercially. Verxite has been approved for use in animal feeds and the U.S. Food and Drug Administration Regulations at 21 Code of Federal Regulations-Subpart C-Sections 121.201 and 121.202. Verxite is a known carrier for some types of nutrients for animal feeds although its use for carrying propionic acid is not known.

The rhyolites, that is such materials as perlite, obsidian, pitchstone and pumice, are also suitable aluminum silicates of the type mentioned in Formula I above which will provide the desired catalytic effect. Perlite, especially an expanded perlite, is an especially good carrier. Like vermiculite, perlite may be thermally exfoliated (expanded) to result in a product having relatively large pores or capillaries, and this expanded product is the preferred form of perlite for use in the present invention.

The carrier material used in the present invention must be in the granular or particulate form to be useful. Generally speaking the particle size should be within the range of about 150 to 2000 microns, preferably within the range of 300 to 1500 microns. Loading of the propionic acid on the carrier material may be easier accomplished by merely spraying the liquid propionic acid unto the particulate carrier material with mixing or tumbling. In order to obtain optimum results the amount of propionic acid absorbed on the carrier material should be such that there are at least about 0.1 part by weight of propionic acid per part by weight of carrier material. The propionic acid should not be loaded on the carrier material to such an extent that the carrier material becomes soggy, sticky or wet to the touch since the particulate carrier material with the propinic acid absorbed thereon needs to be a dry, free-flowing particulate material. The maximum amount of propionic acid that can be loaded onto a carrier material will depend on the particulate carrier material being used. For example, with an unexpanded hydrobiotite up to about 0.25 parts by weight of propionic acid may be loaded onto each part by weight of the hydrobiotite; however, when using verxite, up to about two parts by weight of propionic acid may be loaded onto each part by weight of the verxite. Even though unexpanded hydrobiotite provides the desired catalytic effect of generating monomeric propionic acid, the use of verxite is preferred because of the greater loading capacity per unit weight. The same is true as to expanded perlite. Generally speaking the amount of propionic acid absorbed on the carrier material should be such that there is from about 0.1 to 2, preferably about 0.2 to 1.5 parts by weight of propionic acid per part by weight of carrier material.

When using the aluminum silicates of Formula I as carrier materials, an entirely unexpected and synergistic effect is obtained. That is, the increase in fungicidal efficiency is far in excess of the usual "carrier effect" generally obtained when propionic acid is used on a carrier material instead of being used neat. The use of the carrier material which generates monomeric propionic acid in the vapors can, in fact, present a problem in finding a proper container for storing and shipping the preservative composition of the present invention. Preservative compositions of the type disclosed herein are generally packaged for sale and transportation in commerce in heat sealable bags, low density polyethylene film generally being used because of its low cost and adaptability to heat sealing. Use of a water-tight heat sealed container is generally necessary to prevent the preservative composition from absorbing moisture from the atmosphere. It has been discovered, however, that the preservative compositions of the present invention may not be stored in a low density polyethylene bag since the monomeric propionic acid molecules generated will migrate through the polyethylene film, whereas dimeric propionic acid molecules will not migrate through polyethylene film to any appreciable extent.

The migration of monomeric propionic acid through polyethylene film becomes particularly obvious if the compositions of the present invention are stored in a bag constructed of low density polyethylene film laminated (glued) to a film of a polymer such as polyester (through which the monomeric propionic acid molecules will not escape). With a bag constructed of such a laminate film material with the polyethylene being the inner lining of the bag and the polyester being the outer cover of the bag, droplets of liquid propionic acid will gradually accumulate between the polyethylene-polyester layers. This occurs because the shift of the equilibrium to monomeric propionic acid in the vapors which evaporate from the preservative composition is so great, and the driving force to produce such monomeric propionic acid molecules is so great, that the monomeric propionic acid molecules migrate through the polyethylene until the polyester film is encountered. At this point the monomeric propionic acid will dimerize since it is out of the presence of the catalytic material. Since the dimer cannot migrate back through the polyethylene film, propionic acid molecules become trapped between the layers of polyethylene and polyester which condense to form liquid propionic acid droplets. As pointed out above, liquid propionic acid is highly associated and will be retained by low density polyethylene.

The best bags found for storing and transporting preservative compositions of the present invention are multiwall craft paper bags with an inner layer of either high density polyethylene or aluminum foil. Bags of cross-laminated high-density polyethylene having a 4 mil thickness (2 mil per layer) are also acceptable.

The fact that the monomeric propionic acid molecules will migrate through low density polyethylene film makes it possible to use bags constructed of this film to determine the amount of monomeric propionic acid being formed by one composition as compared to another. Specifically, a preservative composition comprised of propionic acid loaded on a carrier material may be placed in a sealed bag of low density polyethylene film, and the weight of such compositions determined from time to time. Since the bag is sealed, weight loss can only be attributed due to molecules (that is propionic acid monomer) which pass through the polyethylene film. Those which show a relatively fast weight loss will be those having high concentrations of monomeric propionic acid molecules in the vapor phase.

In using the preservative compositions of the present invention, amounts of preservative composition should be admixed with the crop product (or animal feed, etc.) so as to provide from about 0.25 to 2.5 grams of propionic acid per kilogram of crop product. In percentage terms this translates to the propionic acid weight being about 0.025% to 0.25% of the crop product weight. Thus if a preservative composition comprising 50% by weight of propionic acid and 50% by weight verxite were utilized, such preservative composition would be added in amounts of about 0.5 to 5.0 grams per kilogram of crop product to obtain the desired propionic acid level. These levels of propionic acid are generally lower than the levels required by prior art propionic acid compositions for fungicidal activity.

The following examples are given in order to illustrate the present invention but should not be taken as limiting the scope thereof. In the examples, all parts and percentages are by weight unless otherwise indicated.

EXAMPLE I

Two preservative compositions were prepared in accordance with the present invention. One of these preservative compositions was prepared by mixing equal parts of liquid propionic acid and verxite to obtain a dry, particulate composition containing 1 part by weight of propionic acid per 1 part by weight of verxite. The other preservative composition was also prepared by mixing liquid propionic acid with verxite except that only 0.25 parts by weight of propionic acid were utilized per 1 part by weight verxite. These two preservative compositions of the present invention, as well as propionic acid (neat), were tested for mold inhibiting capability in a poultry laying ration. The poultry laying ration was first heated to 150° C. for about six hours and then placed in sterile polyethylene bags. This produced a poultry laying ration with an initial mold count of less than 50,000 colonies per gram. Four of the bags were utilized to test the propionic acid (neat) at varying propionic acid rates, four of the bags were utilized to test the 1/1 propionic acid-verxite composition and four of the bags were utilized to test the 0.25/1 propionic acid-verxite composition. In the case of each of the three fungicides, there was added to one of the bags an amount so as to provide 0.125 grams of propionic acid per kilogram of laying ration, to one of the bags an amount of fungicide to provide 0.375 grams of propionic acid per kilogram of laying ration, to one of the bags an amount to provide 0.5 grams of propionic acid per kilogram of laying ration, and to one of the bags an amount as to provide 0.875 grams of propionic acid per kilogram of laying ration.

After adding the fungicides to the laying ration, the treated rations were then held at room temperature for 40 days. At the end of 40 days the samples were submitted for mold counts. The average mold count for the laying ration treated with propionic acid (neat), that is the average for the four rates of application, was 880,000 mold colonies per gram. The average mold count for the laying ration treated with the 1/1 propionic acid-verxite composition was 228,000 mold colonies per gram and the average mold count for the laying ration treated with the 0.25/1 propionic acid-verxite composition was 410,000 mold colonies per gram. It may thus be seen that the use of the preservative compositions of the present invention gave much better results than propionic acid alone.

Even though the foregoing tests were for a period of 40 days, the use of propionic acid as a preservative, including a propionic acid-containing composition of the present invention, is not recommended for such long periods of time. The present invention is actually recommended only for storage periods up to about 30 days because, after about 30 days, most of the propionic acid will have evaporated and been removed from the presence of the agricultural crop product, etc. by air currents and the like. This of course would not be true if the agricultural crop product were stored in a sealed container but this is not usually the case in industry. Usually animal foodstuffs are fed within about 14 days of their storage.

The verxite utilized in this Example I, as well as all the other examples, was a verxite sold by W. R. Grace & Co. under the brand name "Zonolite". This verxite was identified by W. R. Grace & Co. as size number 4, and had an average bulk density of 6¼ pounds per cubic foot and had a particle size within the range of about 425 to 1180 microns. Further, this verxite was reported to have been produced by thermally expanding hydrobiotite at about 760° C. and reported to have an average mineral content as follows (with the remainder being hydrogen and oxygen):

| | |
|---|---|
| Magnesium | 12.0% |
| Aluminum | 8.0% |
| Iron | 3.25% |
| Silicon | 21.0% |
| Potassium | 4.0% |
| Chromium | 0.11% |
| Barium | 0.8% |
| Calcium | 0.8% |
| Manganese | 0.06% |
| Cobalt | 0.01% |
| Copper | 0.004% |

EXAMPLE II

Propionic acid (neat) and a preservative composition prepared in accordance with the present invention were added to a poultry laying ration in order to determine the efficacy of the present invention in killing healthy mold growth. The poultry ration utilized had an initial mold count of 1,200,000 colonies per gram. The preservative composition prepared in accordance with the present invention consisted of propionic acid absorbed on verxite in a 1/1 ratio. Six samples, with varying propionic acid additive amounts, were utilized to test both the propionic acid (neat) and the preservative composition of the present invention. The amount of fungicide added to the laying ration was such as to provide 0.25 grams per kilogram, 0.5 grams per kilogram, 0.75 grams per kilogram, 1 gram per kilogram, 1.25 grams per kilogram and 1.5 grams per kilogram. Thus in each sample, twice the weight of the propionic acid-verxite composition was added as compared to the propionic acid (neat) in order to give equal quantities of the propionic acid itself. After the fungicides had been added to the treated ration, it was held one week at room temperature and then counted for mold growth. The laying ration which had been treated with the propionic acid (neat) contained an average of 1,098,000 mold colonies per gram while the laying ration treated with the propionic acid-verxite composition contained only 517,000 mold colonies per gram on the average. Thus, it may be seen that the compositions of the present invention are effective not only in inhibiting mold growth as shown in Example I, but are also effective in killing a healthy mold growth.

EXAMPLE III

Three fungicidal mixtures were prepared. One of the fungicidal mixtures consisted of propionic acid absorbed onto ground corn having a particle size in the range of about 250 to 500 microns, there being 0.25 parts of propionic acid per part of ground corn. Two of the fungicial mixtures were prepared in accordance with the present invention and consisted of propionic acid absorbed on verxite, one of the compositions containing 0.25 parts propionic acid per part of verxite and the other containing 1 part propionic acid per part verxite. All three fungicidal compositions were added to a poultry laying ration which had been heated to 150° C. for six hours and then placed in sterile polyethylene bags. The fungicidal mixture was added in varying amounts to each of the three samples such as to provide an amount of propionic acid corresponding to 0.125 grams per kilogram of laying ration, 0.25 grams per kilogram of laying ration and 0.5 grams per kilogram of laying ration. The treated ration was held at room temperature for 40 days and then counted for mold growth. The laying ration which had been treated with propionic acid absorbed on ground corn contained 530,000 mold colonies per gram. The laying ration which had been treated with the 0.25/1 propionic acid-verxite mixture contained 390,000 mold colonies per gram and the laying ration which had been treated with the 1/1 propionic acid-verxite mixture contained only 330,000 mold colonies per gram. It may thus be seen that the present invention provides a kill-rate over and above the "carrier effect" which is obtained when propionic acid is used on a carrier.

EXAMPLE IV

As pointed out above, monomeric propionic acid molecules will migrate through a low density polyethylene film and this may be utilized to determine the relative amounts of monomeric propionic acid molecules present in the vapor above one composition as compared to the vapor above another composition. This may be accomplished by placing different propionic acid containing compositions in sealed low density polyethylene bags and determining the weight loss from each, the weight loss being directly proportional to the amount of monomeric propionic acid in the vapor phase above the composition.

This method was used in order to determine the relative amounts of monomeric propionic acid in the vapor phase above a propionic acid-verxite composition as compared to that above liquid propionic acid. In the experiment three 10×20 cm bags constructed of three mil low density polyethylene were used. In Bag No. 1 was placed 50 grams of a fungicidal mixture consisting of propionic acid-verxite in a 1/1 ratio and the bag then sealed. In Bag No. 2 was placed about 30 grams of liquid propionic acid and the bag then sealed. This left a larger vapor space in Bag No. 2 than Bag No. 1 because of the density of propionic acid being greater than the density of the fungicidal mixture in Bag No. 1. In Bag No. 3, there was placed an amount of propionic acid (about 78 grams) which would cause the vapor space in Bag No. 3, after sealing, to be about the same as that in Bag No. 1. Thus Bag No. 2 contained an amount of propionic acid which was about equal to that in Bag No. 1, while Bag No. 3 had a vapor space about equal to that of Bag No. 1.

The sealed bags were maintained at about 25° to 26° C. for six weeks and weighed weekly in order to determine weight loss due to monomeric propionic acid molecules passing through the polyethylene film. The percentage of propionic acid lost was then calculated, the results being set forth in Table I following:

TABLE I

| Week | Propionic Acid Lost, % | | |
|---|---|---|---|
| | Bag No. 1 | Bag No. 2 | Bag No. 3 |
| 0 | 0 | 0 | 0 |
| 1 | 12 | 8 | 4 |
| 2 | 24 | 19 | 9 |
| 3 | 37 | 27 | 13 |
| 4 | 47 | 34 | 17 |
| 5 | 55 | 45 | 22 |
| 6 | 68 | 53 | 26 |

As may be seen from Table I, Bag No. 1 containing the propionic acid-verxite composition lost a far greater amount of propionic acid than the bags containing the liquid propionic acid. This indicates that the amount of monomeric propionic acid in the vapor above the propionic acid-verxite composition was far greater than that above propionic acid alone.

It has been reported in the literature that, at equilibrium at 25° C., 19% of the propionic acid in the vapor above the liquid is in the monomeric form, the remaining 81% being in the dimeric form. Based on the results of the foregoing experiment (that is, on the weight loss after six weeks), this would indicate that at least 24% of the propionic in the vapor in Bag No. 1 was in the monomeric form. That is, if 19% monomer in the vapor phase resulted in the 53% loss of Bag No. 2, then 24% monomer in the vapor phase would result in the 68% loss of Bag No. 1. The same results may be arrived at by using the results after two weeks.

EXAMPLE V

In accordance with the procedure of Example IV, the amount of monomeric propionic acid in the vapor above propionic acid absorbed onto ground corn was compared to the amount of monomeric propionic acid in the vapor above propionic acid absorbed on verxite. In Bag No. 1 was placed 50 grams of a fungicidal composition consisting of 10 grams propionic acid absorbed on 40 grams of ground corn. In Bag No. 2, there was placed 250 grams of a fungicidal composition consisting of 50 grams propionic acid absorbed on 200 grams ground corn. Bag No. 3 contained 50 grams of a fungicidal composition consisting of 10 grams propionic acid absorbed on 40 grams verxite. The particle size of the corn was within the range of about 250 to 500 microns but the corn was more dense than the verxite. Thus, Bags Nos. 1 and 3 compared equal weights of materials and Bags Nos. 2 and 3 compared equal volumes of material. The sealed bags were stored at room temperature (about 25° C.) and weighed periodically in order to determine weight loss (proponic acid loss). The results are set forth in the following Table II:

TABLE II

| Week | Propionic Acid Lost, % | | |
|---|---|---|---|
| | Bag No. 1 | Bag No. 2 | Bag No. 3 |
| 0 | 0 | 0 | 0 |
| 1 | 13 | 4 | 35 |
| 2 | 26 | 11 | 66 |
| 3 | 35 | 16 | 85 |
| 4 | 44 | 20 | 96 |

From the foregoing Table II it may be seen that the amount of monomeric propionic acid in the vapors above the propionic acid-verxite of Bag No. 3 was much greater than that above the compositions of Bags Nos. 1 and 2. When compared to the results of Example IV, it may be appreciated that the amount of monomeric acid in the vapor above the ground corn was even less than that above liquid propionic acid, that is even less than 19% monomer at about 25° C. It is estimated that the propionic acid in the vapor phase above the ground corn was probably no greater than 10 to 11% monomer. Since ground corn is not only a suitable carrier for propionic acid but is also a type of processed agricultural product which may be, and is, preserved by spraying propionic acid (neat) thereon, this Example IV indicates that when treating an agricultural product with propionic acid (neat), only about 10 to 11% of the propionic acid in the vapors will be in the monomeric form.

EXAMPLE VI

An experiment was performed to determine whether or not the increase in fungicidal activity of propionic acid-verxite compositions could be due to an increased evaporation rate of the propionic acid instead of increased amounts of monomeric propionic acid in the vapor. To check this possibility there was placed in an open beaker 31 grams of a fungicidal composition consisting of 6 grams propionic acid absorbed on 25 grams ground corn. In another open beaker there was placed 31 grams of a fungicidal composition consisting of 6 grams of propionic acid absorbed on 25 grams verxite. The beakers were stored at room temperature and weighed periodically in order to determine weight loss. Since the beakers were open, practically all weight loss would be due to evaporation of propionic acid, regardless of whether it was in the monomeric or dimeric form. After two days about 42%, and after nine days about 85% of the propionic acid on the propionic acid-verxite composition had been lost. On the contrary, the propionic acid-ground corn composition lost about 77% of the propionic acid after two days and about 96% after nine days. Thus the evaporation rate from ground corn was ever greater than that from verxite even though the ground corn had less fungicidal activity.

EXAMPLE VII

The procedure of Example V was repeated except that Bag No. 1 contained 30 grams of a fungicidal composition consisting of 5 grams propionic acid absorbed on verxite; Bag No. 2 contained 30 grams of a fungicidal composition consisting of 5 grams propionic acid absorbed on unexpanded hydrobiotite; and, Bag No. 3 contained 30 grams of a fungicidal composition consisting of 5 grams propionic acid absorbed on 25 grams ground corn. The results are shown in the following Table III:

TABLE III

| Day | Propionic Acid Lost, % | | |
| --- | --- | --- | --- |
|  | Bag No. 1 | Bag No. 2 | Bag No. 3 |
| 0 | 0 | 0 | 0 |
| 2 | 19 | 19 | 11 |
| 5 | 42 | 42 | 25 |
| 8 | 64 | 64 | 37 |
| 12 | 86 | 88 | 52 |
| 14 | 92 | 96 | 58 |
| 16 | 93 | 97 | 63 |

From a comparison of the results regarding Bags Nos. 1 and 2, it may be seen that an unexpanded hydrobiotite gives substantially the same results as an expanded hydrobiotite, thus discounting any surface effect and indicating that the generation of monomeric propionic acid is truely a catalytic effect. Of course an expanded hydrobiotite is prefered since the amount of propionic acid that may be loaded onto an expanded hydrobiotite is much greater than an unexpanded hydrobiotite.

EXAMPLE VIII

The procedure of Example IV was used in order to determine the relative amounts of monomeric propionic acid in the vapor phase above a propionic acid-verxite composition as compared to that above a propionic acid-expanded perlite composition. In the experiment four 10×20 cm bags constructed of three mil low density polyethylene were used. In each of Bag No. 1 and Bag No. 2 was placed 23 grams of a mixture consisting of 8 grams of propionic acid absorbed onto 15 grams of expanded perlite. In each of Bag No. 3 and Bag No. 4 there was placed 23 grams of a composition consisting of 8 grams propionic acid absorbed onto 15 grams of verxite. The verxite corresponded to that utilized in Example I. The expanded perlite was reported to have been produced by thermally expanding perlite at about 825° to 1100° C. and reported to have a typical chemical analysis as follows, all percentages being in weight percent:

| Silica | $SiO_3$ | 72.39% |
| --- | --- | --- |
| Alumina | $Al_2O_3$ | 13.95% |
| Iron Oxide | $Fe_2O_3$ | .73% |
| Lime | $CaO$ | .57% |
| Magnesia | $M_gO$ | .46% |
| Sodium Oxide | $Na_2O$ | 3.92% |
| Potassium Oxide | $K_2O$ | 4.07% |
| Sulphur Trioxide | $SO_3$ | .003% |
| Carbon Dioxide | $CO_2$ | .0018% |
| Loss on Ignition | $H_2O$ | 3.85% |

The expended perlite was also reported to have an average bulk density of 7.5 to 12 pounds per cubic foot and a particle size within the range of about 125 to 1400 microns. The sealed bags were stored at room temperature (about 25° C.) and weighed periodically in order to determine weight loss (propionic acid loss). The results are set forth in the following Table IV.

TABLE IV

| Day | Propionic Acid Lost, % | | | |
| --- | --- | --- | --- | --- |
|  | Bag No. 1 | Bag No. 2 | Bag No. 3 | Bag No. 4 |
| 4 | 20.4 | 20.7 | 18.4 | 20.1 |
| 7 | 29.3 | 30.2 | 26.4 | 28.6 |
| 10 | 50.2 | 51.6 | 45.5 | 49.0 |
| 12 | 67.5 | 69.4 | 62.0 | 66.2 |
| 19 | 82.6 | 84.2 | 77.0 | 81.5 |
| 25 | 94.4 | 96.2 | 90.9 | 95.0 |

From a comparison of the results regarding Bags Nos. 1 and 2 as compared to Bags Nos. 3 and 4, it may be seen that expanded perlite gives substantially the same results as verxite in generating monomeric propionic acid.

EXAMPLE IX

An experiment was performed in order to determine the effectiveness of propionic acid absorbed onto expanded perlite as a fungicidal composition. The expanded perlite was the same expanded perlite as utilized in Example VIII above. The experiment was conducted on cracked corn having 23% by weight of moisture. To one sample of 200 grams of the cracked corn there was added 0.3 grams of a mixture consisting of propionic acid absorbed on expanded perlite in a 1/1 weight ratio. To a second sample of 200 grams of the cracked corn was added 0.15 grams of liquid propionic acid. A third sample of 200 grams of the cracked corn was not treated with any preservative and served as a control. All three samples were then stored at room temperature (about 25° C.) and observed daily for an indication of fungal activity. The first sample containing the propionic acid-perlite composition did not show any noticeable fungal activity until about 22 days. The second sample treated with the liquid propionic acid (neat) showed noticeable fungal activity after only 10 days, and the untreated third sample showed noticeable fungal activity after only 5 days.

From the foregoing, it appears that propionic acid (neat) and the propionic acid-carrier compositions of the prior art would not, at 25° C., catalyze and effect the formation of propionic acid in the monomeric form. In fact it appears that the amount of monomeric propionic acid might even be decreased by prior art carriers below that existing in the vapor above liquid propionic acid at 25% C. Preferably, the carrier material is one which, at 25° C., will catalyze and effect the formation of propionic acid in the propionic acid vapors to such an extent that at least about 22 wt. percent of the propionic acid in the vapors is in the monomeric form. This 22% is well above the amount existing when propionic acid is used neat and well above prior art propionic acid-carrier compositions.

Based on the discoveries herein disclosed, undoubtedly new and useful carrier materials which will catalyze the formation of monomeric propionic acid will be discovered other than the particular types of aluminum silicates herein mentioned; and, the present invention is not to be construed as limited to these particular types of aluminum silicates as carriers.

The embodiments of the invention in which an exclusive property or privilege is claimed are defined as follows:

1. A dry, free-flowing particulate composition useful as a preservative for a product consisting essentially of a raw or processed agricultural crop product which is subject to microbiological degradation, which is low in sugars and high in one or more of cellulose, starch or lignin, and which product contains moisture, said particulate composition comprising verxite in particulate form having absorbed thereon from about 0.1 to about 2.0 parts by weight of propionic acid in the liquid form per part by weight of said verxite, and wherein the particle size of said verxite is within the range of from 150 to 2000 microns.

2. The composition of claim 1 wherein said particle size of said verxite is within the range of from about 300 to 1500 microns.

3. The composition of claim 2 wherein there is from about 0.2 to 1.5 parts by weight of propionic acid in the liquid form per part by weight of said verxite.

4. The composition of claim 3 wherein said agricultural crop product is a processed agricultural crop product which is an animal foodstuff.

5. The composition of claim 3 wherein said agricultural crop product is cereal grain.

6. A dry, free-flowing particulate composition useful as a preservative for a product consisting essentially of a raw or processed agricultural crop product which is subject to microbiological degradation, which is low in sugars and high in one or more of cellulose, starch or lignin, and which product contains moisture, said particulate composition comprising an expanded perlite which has been produced by thermal exfoliation in particulate form having absorbed thereon from about 0.1 to about 2.0 parts by weight of propionic acid in the liquid form per part by weight of said expanded perlite, and wherein the particle size of said expanded perlite is within the range of from 150 to 2000 microns.

7. The composition of claim 6 wherein said particle size of said expanded perlite is within the range of from about 300 to 1500 microns.

8. The composition of claim 7 wherein there is from about 0.2 to 1.5 parts by weight of propionic acid in the liquid form per part by weight of said expanded perlite.

9. The composition of claim 8 wherein said agricultural crop product is a processed agricultural crop product which is an animal foodstuff.

10. The composition of claim 8 wherein said agricultural crop product is cereal grain.

11. A composition having improved storage characteristics comprising a raw or processed agricultural crop product which is subject to microbiological degradation and which is low in sugars and high in one or more of cellulose, starch and lignin and which contains moisture, admixed with a fungus-inhibiting amount of a dry, free-flowing particulate composition comprising verxite in particulate form having absorbed thereon from about 0.2 to 1.5 parts by weight of proprionic acid in the liquid form per part by weight of said verxite, the particle size of said verxite being within the range of from about 150 to 2000 microns, and wherein the amount of said particulate composition admixed with said product is such as to provide from about 0.25 to 2.5 grams propionic acid per kilogram of said product.

12. A composition having improved storage characteristics comprising a raw or processed agricultural crop product which is subject to microbiological degradation and which is low in sugars and high in one or more of cellulose, starch and lignin and which contains moisture, admixed with a fungus-inhibiting amount of a dry, free-flowing particulate composition comprising and expanded perlite which has been produced by thermal exfoliation in particulate form having absorbed thereon from about 0.2 to 1.5 parts by weight of propionic acid in the liquid form per part by weight of said expanded perlite, the particle size of said expanded perlite being within the range of from about 150 to 2000 microns, and wherein the amount of said particulate composition admixed with said product is such as to provide from about 0.25 to 2.5 grams propionic acid per kilogram of said product.

13. A method of inhibiting fungus growth in a product consisting essentially of a raw or processed agricultural crop product which is subject to microbiological degradation, which is low in sugars and high in one or more of cellulose, starch and lignin, and which contains moisture, said method comprising intimately admixing with said product a fungus-inhibiting amount of a dry, free-flowing particulate composition comprising verxite in particulate form having absorbed thereon from about 0.1 to about 2.0 parts by weight of propionic acid in the liquid form per part by weight of said verxite; the particle size of said verxite being within the range of from about 150 to 2000 microns, and wherein there is admixed with said product an amount of said particulate composition which will provide from about 0.25 to 2.5 grams of propionic acid per kilogram of said product.

14. The method of claim 13 wherein said verxite has a particle size within the range of from about 300 to 1500 microns and wherein there is from about 0.2 to 1.5 parts by weight of propionic acid in the liquid form per part by weight of said verxite.

15. The method of claim 14 wherein said agricultural crop product is a processed agricultural crop product which is an animal foodstuff.

16. The method of claim 14 wherein said agricultural crop product is cereal grain.

17. The method of claim 13 wherein said agricultural crop product is a processed agricultural crop product which is an animal foodstuff.

18. A method of inhibiting fungus growth in a product consisting essentially of a raw or processed agricultural crop product which is subject to microbiological degradation, which is low in sugars and high in one or more of cellulose, starch and lignin, and which contains moisture, said method comprising intimately admixing with said product a fungus-inhibiting amount of a dry, free-flowing particulate composition comprising an expanded perlite which has been produced by thermal exfoliation in particulate form having absorbed thereon from about 0.1 to about 2.0 parts by weight of propionic acid in the liquid form per part by weight of said expanded perlite; the particle size of said expanded perlite being within the range of from about 150 to 2000 microns, and wherein there is admixed with said product an amount of said particulate composition which will provide from about 0.25 to 2.5 grams of propionic acid per kilogram of said product.

19. The method of claim 18 wherein said expanded perlite has a particle size within the range of from about 300 to 1500 microns and wherein there is from about 0.2 to 1.5 parts by weight of propionic acid in the liquid form per part by weight of said expanded perlite.

20. The method of claim 19 wherein said agricultural crop product is cereal grain.

* * * * *